(12) United States Patent
Zaldivar et al.

(10) Patent No.: US 6,425,686 B1
(45) Date of Patent: Jul. 30, 2002

(54) GLASS TRANSITION TEMPERATURE MEASUREMENT SYSTEM

(75) Inventors: Rafael J. Zaldivar, Huntington Beach; James P. Nokes; Gary F. Hawkins, both of Torrance, all of CA (US)

(73) Assignee: The Aerospace Corporation, El Segundo, CA (US)

( * ) Notice: Subject to any disclaimer, the term of this patent is extended or adjusted under 35 U.S.C. 154(b) by 195 days.

(21) Appl. No.: 09/590,608

(22) Filed: Jun. 9, 2000

(51) Int. Cl.[7] .......................... G01N 25/00; G01N 1/00
(52) U.S. Cl. .......................... 374/16; 374/22; 374/23; 374/49; 374/51; 73/78; 73/81
(58) Field of Search .......................... 374/16, 22, 23, 374/51, 49; 73/78, 81, 85

(56) References Cited

U.S. PATENT DOCUMENTS

| | | | | |
|---|---|---|---|---|
| 1,184,837 A | * | 5/1916 | Edgecomb | |
| 3,597,965 A | * | 8/1971 | Kawamura et al. | 73/81 |
| 4,259,860 A | * | 4/1981 | Labino | 73/17 R |
| 4,266,424 A | * | 5/1981 | Mueustedt | 73/15.6 |
| 4,506,547 A | * | 3/1985 | Kunze et al. | 73/150 R |
| 4,508,460 A | * | 4/1985 | Croo | 374/16 |
| 4,611,487 A | * | 9/1986 | Krenn et al. | 73/81 |
| 4,852,397 A | * | 8/1989 | Haggag | 73/82 |
| 5,357,786 A | * | 10/1994 | Lung et al. | 73/81 |
| 6,227,703 B1 | * | 5/2001 | DiMatteo et al. | 374/208 |
| 6,231,228 B1 | * | 5/2001 | Brotz | 374/17 |
| 6,247,355 B1 | * | 6/2001 | Suresh et al. | 73/82 |

* cited by examiner

Primary Examiner—Diego Gutierrez
Assistant Examiner—Gail Verbitsky
(74) Attorney, Agent, or Firm—Derrick Michael Reid

(57) ABSTRACT

A glass transition temperature Tg measurement system includes a probe point penetrating into a sample under test that has been heated by a heater to a temperature where the sample undergoes a phase change from a solid to a semi-solid. A thermocouple is used to measure the temperature while a motion transducer is used to measure the amount of penetration. The penetration amount sharply increases at the glass transition temperature. A portable unit can be used in the field to test the Tg properties of various composite materials used, for example, in structures including buildings and bridges.

11 Claims, 3 Drawing Sheets

Tg TESTING APPARATUS

Tg TESTING APPARATUS

PORTABLE Tg TESTER

DISPLACEMENT-TEMPERATURE PROFILE

GLASS TRANSITION TEMPERATURE MEASUREMENT SYSTEM

FIELD OF THE INVENTION

The invention relates to the field of material properties. More particularly, the present invention relates to the testing of the glass transition property of composite glass materials.

BACKGROUND OF THE INVENTION

Composite materials having desirable mechanical properties have been used to structurally reinforce and repair thousands of highway columns and bridges. Epoxy matrix composites are the material-of-choice, usually with carbon and/or glass fiber reinforcement. Quality control techniques are desirable to validate and ensure the soundness of these new structures. Reliable and efficient quality control techniques are essential for cost effective field testing. The degree of cure of the resin matrix used will have a pronounced effect on the final mechanical and thermal properties of the composite. Factors that may affect the degree of cure, such as lower-than-expected thermal exposure, excessive post-cure temperatures, contamination, moisture or solvent exposure, improper component mixing, and nonstoichiometric epoxy hardener formulations will also have a direct effect on the glass-transition temperature (Tg) of the composite. The resin material undergoes a solid to a semisolid phase transition at Tg. The elastic modulus of some polymers may decrease by over a thousand times as the temperature is raised through the Tg. For this reason, Tg can be considered the most important material property of a polymer. By identifying the Tg of a composite material after fabrication, validation of a complete cure can be verified. In addition, the Tg of the composites can be monitored in conjunction with other non-destructive evaluation techniques over the lifetime of the structure to provide reliability.

Many different composite systems and fabrication test techniques may be used. The composites can be fabricated by infiltrating the liquid resin into the reinforcement and then hoop winding the tows/fabric onto the large concrete columns. The composites are also being applied to the tensile side of support beams. The composites can also be laid-up by hand and/or wrapped as infiltrated tape. Most of the epoxy resins used in these composites require only room-temperature cure to fully crosslink and reach a suitable degree of cure, greater than 85% for their required application. However, the thermal and mechanical limits of these composites are often much lower than that of resins that require elevated temperature cure processing. This upper thermal limit is controlled by the glass-transition temperature, Tg, of the resin. The glass transition temperature Tg is the temperature at which the material undergoes a solid to semisolid phase transition. At this temperature, the elastic modulus may decrease by over 1000 times as the temperature is raised through this region. The Tg of the resin is controlled by the inherent chemical structure of the resin, the degree of crosslinking or cure the resin has experienced, and whether it has been exposed to any environmental and/or contamination species that may affect the primary polymerization reaction. Therefore, the contractors must ensure that they use resin materials in their composites that have sufficiently high glass-transition temperatures for the application, and that the selected material reaches a sufficiently high degree of cure or polymerization to achieve this Tg upper limit. A lower than expected Tg will signal problems associated with processing or environmental exposure.

Quality control techniques must be developed and are necessary to validate and ensure the soundness of these new composite structures. These techniques are especially essential for field testing. A low Tg can be the result of a lower-than-expected thermal cure treatment, excessively high post-cure temperature exposure, contamination, moisture or solvent exposure, improper component mixing, and non-stoichiometric epoxy to hardener formulations. This report discusses some promising preliminary tests that have been performed to quickly verify the glass-transition temperature of these structural composites after processing and throughout their lifetime.

The ultimate Tg of a material is controlled by the chemical structure, the degree of polymerization, and-contamination or plastization prior to or after cure. The most important factor is chain stiffness or flexibility of the polymer. Long aliphatic groups increase flexibility and lower the Tg. Rigid groups, such as aromatic structures and pendant tertiary butyl groups tend to raise the Tg. The Tg is effected by decreasing the molecular. flexibility by the substitution of bulky side groups onto a polymer chain, for example, polyethylene has a Tg of −120 C., polypropylene has a Tg of −10° C., polystyrene has a Tg of 100° C., and two-six polydichlorostyrene has a Tg of 176° C. A second factor is the backbone symmetry of the polymer. Unsymmetrical polymers are more likely to have a higher Tg than the symmetrical polymers. The greater the impedance to bond rotation for unsymmetrical polymers increases their glass transition temperature compared with symmetrical structures. The Unsymmetrical composite is illustrated by the pairs of polymers, for examples, polypropylene has a Tg of 10° C. and polyisobutlylene has a Tg of −70°, and polyvinylchloride has a Tg of 87° C. and polyvinylidene chloride has a Tg of −19° C. However, within the same resin system, the greatest effect on Tg will be related to the degree of cure or crosslinking the resin has experienced. As the crosslinking sites increase, the polymer introduces restrictions on the molecular motion of the chains. These restrictions cause an increase in the resultant Tg. For example, in the case of an epoxy resin, if the resin material in the composite is poorly cured or has not experienced sufficient crosslinking during processing, a lower than expected Tg will indicate processing problems.

The elastic modulus of the resin material provides variations across the glass-transition temperature range. Typical standard Tg analysis tests usually take twenty to thirty minutes. However, other physical properties have also been observed to change rapidly. The thermal expansion, the heat capacity, the mechanical damping behavior, the electrical properties, the nuclear magnetic resonance behavior, and the refractive index all change abruptly through the Tg. Therefore, there are numerous techniques that have been developed to identify the Tg of polymer resins. However, there are disadvantages to many of these techniques, especially with respect to testing composites in the field. Dynamic mechanical analysis is one of the most commonly used. Dynamic mechanical analysis measures the response of a material to sinusoidal or other periodic stress. Because the stress and strain are usually not in phase, two quantities, a modulus and phase angle or damping term can be determined. Because the material usually undergoes a large drop in modulus through the glass-transition temperature, the instrument can identify the Tg point. In addition, the damping variable or viscous component of the material reaches a maximum through this transition and is also easily identified.

The samples for testing may be cut to some specified dimensions and held between two grips while tested under a torsional shear mode. The tests are performed from tag ends or by destructive evaluation of the part to be tested. The test is usually not suited for out-of-laboratory testing. The advantage of this testing mode is that tests can be performed at a range of frequencies and temperatures. Depending on the frequency used, very subtle secondary transitions can also be identified. These secondary transitions are related to the physical and chemical structure of the resin and have been correlated with properties such as impact strength and toughness. A disadvantage of the Dynamic mechanical analysis method is the required use of a gripping apparatus that cannot be easily used in the field.

A second commonly used test is differential scanning calorimetry. Differential scanning calorimetry is a technique that is designed to measure the amount of energy absorbed or given off by a material as a function of temperature. Temperature differences between the sample and an inert reference sample are recorded as a function of the sample temperature, with the area under the output curve being directly proportional to the total energy transferred into and out of the sample. The ordinate of the resultant thermogram is proportional to the rate of heat transfer at any give time. Because there are changes in the heat capacity of resin samples through the glass-transition temperature, a shallow endothermic peak is usually indicative of this point in a thermosetting resin. Unlike melting-point endotherms and heat of reaction polymerization exotherms, Tg transitions are typically much more subtle in nature. Therefore, the Tg endotherm is not easily identified and is subject to error. A typical DSC scan is taken at a thermosetting resin post-cured under preconditions, such as isothermal post-cure. The Tg for the resin post-cured is well defined. The sample that has been cured for the longer period of time has a Tg that is indistinguishable by differential scanning calorimetry. In a composite, the amount of resin material tested is further minimized by the volume fraction of the fiber reinforcement, leading to even more difficult resolution of the Tg endotherm.

A third test method that can be used is dielectric analysis of the resin material. A sample is treated as a capacitor, and an alternating field is applied to the material as a function of temperature to identify changes in permeativity and dielectric constant. This dielectric test is ideal for insulating resins and can be performed at numerous frequencies. However, only non-carbon, fiber-reinforced composites can be tested. Carbon-fiber-reinforced resins, which are typically used in structural applications, cannot be tested due to the overwhelming conductive nature of carbon fibers. A thermal expansion experiment can also be performed to identify the Tg of the material. The Tg can be observed as a distinct change in the slope of the thermal expansion of the material when passing through the Tg. The dielectric test method can identify the Tg of resins, but with composite materials, factors such as the fiber volume, the fiber orientation, the lay-up configuration, and porosity usually overwhelm the response for Tg identification.

There are other tests that measure or can help identify Tg through indirect correlation. For example, spectroscopy measurements such as nuclear magnetic resonance, Fourier transform infrared, and Raman spectroscopy can identify the formation or disappearance of specific chemical groups in the resin during polymerization. By following the consumption or formation of certain species, the degree of cure can be assessed. The degree of cure can then be correlated to the Tg of the composite measured. There are portable spectroscopy units that have been used for these applications. However, very detailed correlation graphs must be developed for each of the resin systems to be tested and used in the composite structure. In addition, the fibers usually interfere with the signal. Large differences in the degree of cure may be discernible, but subtle variations during the later stages of cure may not be easily identified. The Tg of a resin material usually shows the largest change during the final stages of cure, which for spectroscopy are the shifts most difficult to identify.

Another test that can be used to approximate the Tg of unfilled resins is the heat distortion temperature test method. Most plastics, except for a few thermosetting resins, soften at some temperature. At the softening or heat distortion temperature, the material softens quickly and deforms under load. Above the heat distortion temperature, rigid polymers, such as epoxies become useless as structural materials. As expected for amorphous resins, the heat distortion temperature is closely related to the Tg. However, in composite systems, such as fiber reinforced systems, particulate matrix system, the heat distortion temperature can be substantially higher than the Tg. The reinforcement stiffens the material and makes the material resistant to mechanical deflection. Thus, if the entire sample is tested under load and depending on the fiber volume and architecture of the reinforcement, the sample may resist deformation to a higher temperature than the Tg of the resin. Separating these effects or deemphasizing the mechanical effect of reinforcement would allow for a more ideal testing situation. The prior test systems and method generally require ideal conditions, ideal materials and complex testing apparatus. These and other disadvantages are solved or reduced using the invention.

SUMMARY OF THE INVENTION

An object of the invention is to provide a system for measuring the glass transition temperature of a material.

Another object of the invention is to provide a system for measuring the glass transition temperature of a composite material.

Yet another object of the invention is to provide a system for measuring the glass transition temperature of a composite material using a penetrating probe tip applied to the composite material at a measured temperature.

The present invention is directed towards a system to measure the glass-transition temperature Tg of structural composites. The Tg identification system provides a direct measurement of Tg without being affected by the type of reinforcement used in the composite. The system provides a thermal scan indentation by which a small pin-head probe is placed on the sample surface. Displacement of the probe into the sample is monitored as the temperature is scanned from room temperature to above the predicted glass-transition temperature of the composite. The system should limit probe penetration, for example, less than 0.2 mm, in order to minimize the effect of the reinforcement. As a portable unit, the system can determine the Tg of composite materials in situ. These and other advantages will become more apparent from the following detailed description of the preferred embodiment.

DETAILED DESCRIPTION OF THE PREFERRED EMBODIMENT

Figure 1:
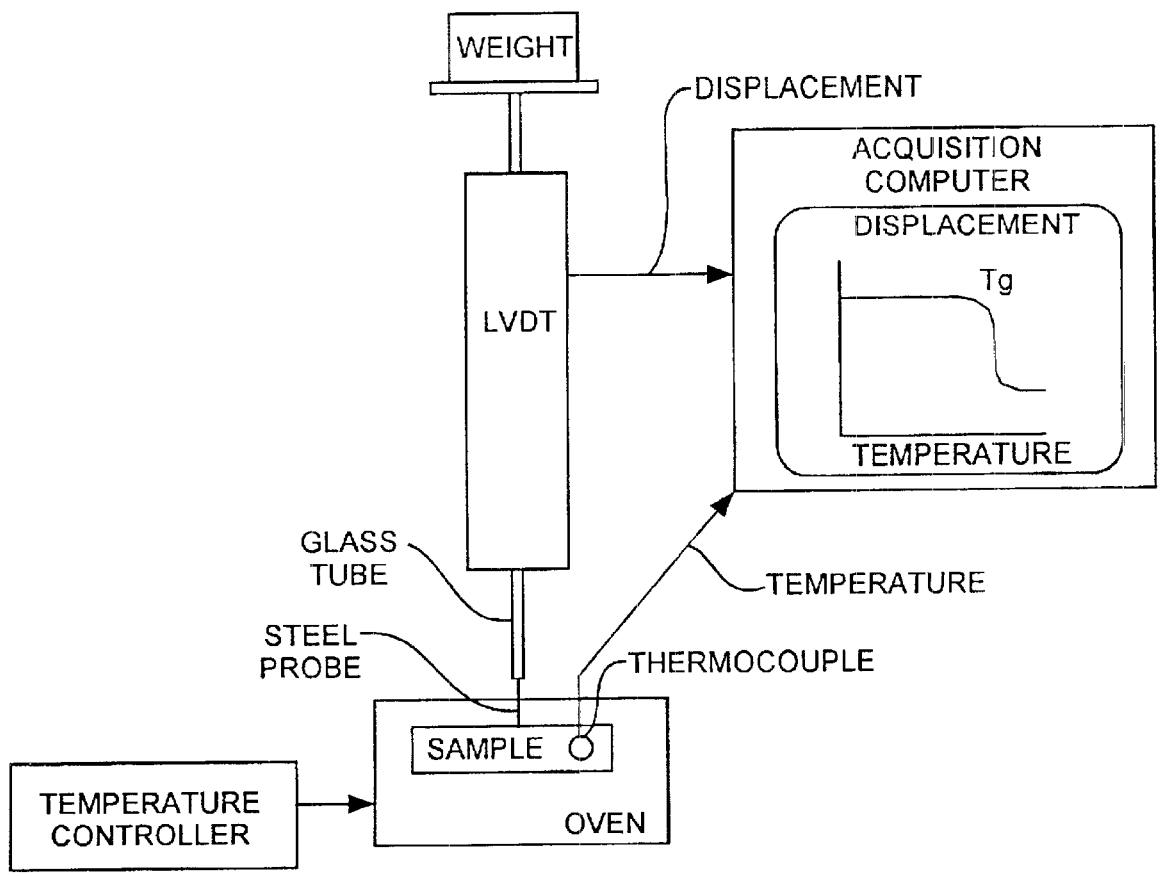
FIG. 1 is a diagram of a Tg testing apparatus.

An embodiment of the invention is described with reference to the figures using reference designations as shown in the figures. Referring to FIG. 1, A glass transition testing apparatus is shown having a steel probe penetrating a sample to be tested. A temperature controller controls the temperature of the sample disposed in an oven. A thermocouple is used to provide a temperature reading of the sample. A weight provides a load force through a glass tube to the probe. A linear variable displacement transducer, LVDT, provides a displacement measurement. An acquisition computer receives displacement and temperature reading as various points to generate a displacement-temperature curse for defining the Tg point of the sample.

Figure 2:
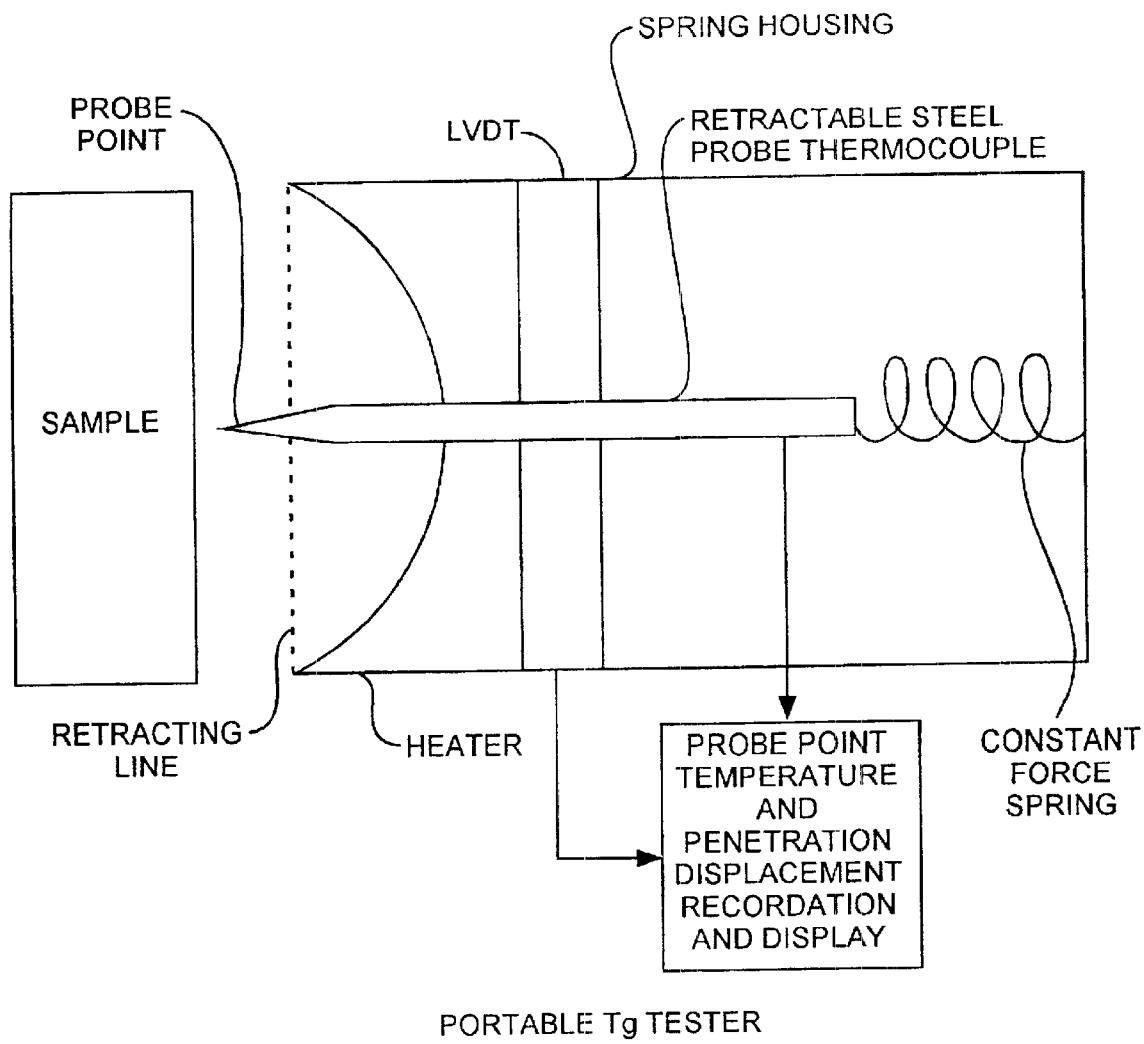
FIG. 2 is a diagram of portable Tg tester having a testing probe and thermocouple for measuring penetration depth and temperature.

Referring to FIG. 2, a portable Tg tester is shown, having a temperature and displacement display. A constant force spring is used to provide the load force. A retractable steel probe and thermocouple extends from the spring. The thermocouple measures the temperature at the top of the retractable steel probe. The spring is disposed in a spring housing affixed to an inductive transducer (LVDT) for providing the displacement display. The probe has a probe point for penetration into a sample. A retracing line is defined by an aperture at the end of the tester where a heater is disposed to heat the sample. The retracing line defines the extent of penetration.

Figure 3:
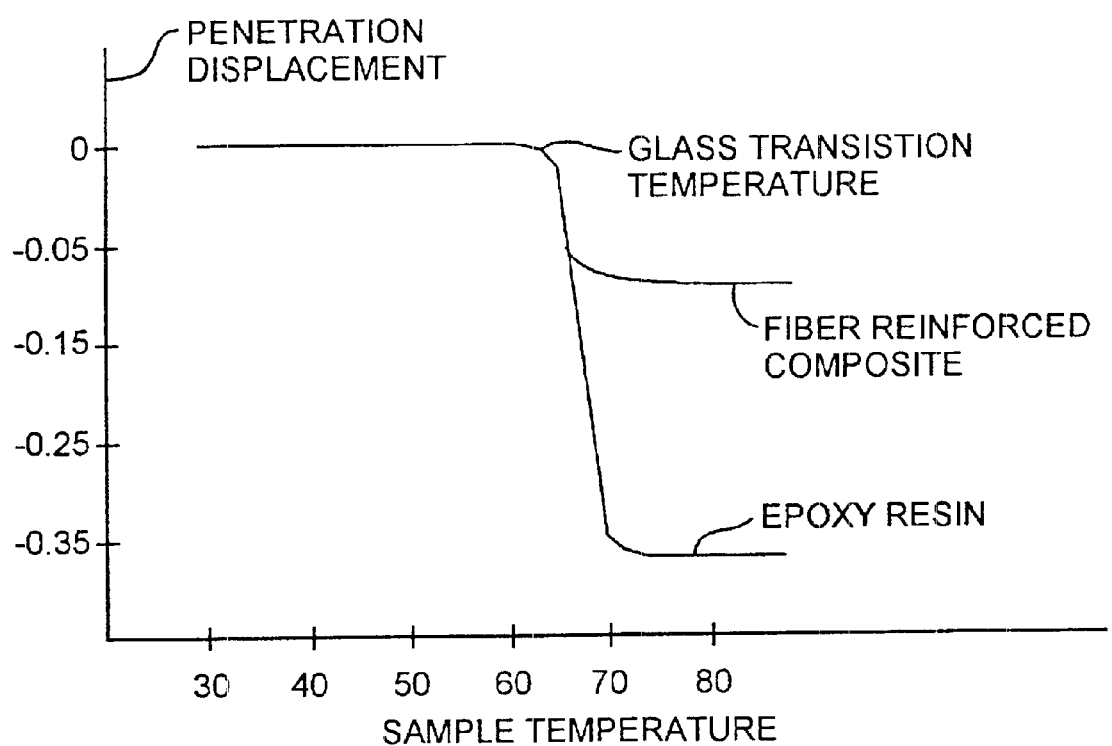
FIG. 3 is a displacement-temperature graph depicting the Tg point at a particular probe penetration depth and temperature.

Referring to all of the Figures, and more particularly to FIG. 3, the penetration depth into the sample can be plotted as a function of temperature of the sample being tested. As the temperature of the sample increases, the phase of the sample changes. When the phase of the sample changes from a solid to a semisolid, the probe point begins to penetrate into the sample material. At that solid to semisolid transition temperature, the penetration amount begins to increase as well as defining the glass transition temperature. The graph exhibits test results obtained using a system on both neat resin and a carbon fiber-reinforced composite using the same resin as the matrix material. As shown, the displacement is constant from room temperature until it reaches the apparent Tg of the resin. At this point, the material shows a distinct decrease in displacement. The resin material shows a much larger amount of total displacement than the composite. However, the magnitude of the displacement does not appear to be of any importance, only the temperature of the transition matters. Both the neat resin and the composite yield the same Tg, as expected. The Tg to be identified is at the inflection or bend in the penetration-temperature curve. The Tg measured for this material using a dynamic mechanical analysis was 65° C., which agrees very well with this technique. A variability of ±5° C. is acceptable for most Tg identification tests The sample may be heated by an oven or by a contact heater with the probe disposed on the surface of the sample. The sample is typically heated at a predetermined rate over a temperature range. The probe may be connected to the core of the LVDT position sensor with a load applied, for example, a 100 gram load. The thermocouple is disposed in proximity to the probe for measuring the temperature of the sample. The temperature cycle may take less than five minutes for most composite materials and a one minute heating cycle may be used. A real-time plot of probe displacement versus temperature is recorded during the test. A data acquisition program is used to collect and graph the data. The Tg glass transition point is determined at the point of inflection in the curve. The portable system is preferably spring loaded with an optimized probe diameter. The heat source couple heat through convection or through contact. The same Tg is determined from a neat epoxy resin or a fiber-reinforced composite utilizing the same resin as the matrix material. The loads can vary loads, for examples, from 50 to 2000 grams. However, there is minimal effect due to variations in the load. The largest variation is that of the total displacement experienced by the probe at Tg for the different weights. The magnitude of the probe displacement is:not determinative, but rather the Tg temperature at the glass transition point.

The heating rate has an effect on the apparent Tg of resins and glasses. The glass-transition temperature is generally measured by experiments that correspond to a time scale of seconds or minutes. If the experiment is performed rapidly, so that the time scale is shortened, the apparent Tg is raised. If the time scale is lengthened to hours or days, the apparent Tg is lowered. Thus, as generally measured, the Tg is not a true constant but shifts with time. Changing the time scale by a factor of 10 will usually shift the Tg by roughly 7° C. for a typical polymer. The Tg is raised as the heating rate is increased. There is also a stepwise drop in displacement that is magnified as the heating rate is decreased. The temperature increase rate should be selected so that the apparent Tg is equal to the actual Tg. The dependence of Tg on heating rates with the thermal scan indentation technique is consistent with standard Tg measurement techniques. A temperature rate of 25° C./min is typically slow enough to provide Tg measurement that can be related to the actual Tg of the sample.

The present system enables a quality control method for the determination of Tg to validate and ensure the soundness of structures fabricated from composite materials and that they have been processed properly. The test can be used to determine whether a fiber-reinforced composite has been processed to the correct degree of cure for optimal properties, and can be used to determine whether environmental factors have caused degradation of the matrix material over the lifetime of the structure.

The system operates relatively fast due to the simplicity and excellent resolution. The amount of the load has a minimal effect on the detection of the Tg. The test duration is approximately five minutes and is ideal for portable applications. The variability is approximately 3–5° C. Those skilled in the art can make enhancements, improvements, and modifications to the invention, and these enhancements, improvements, and modifications may nonetheless fall within the spirit and scope of the following claims.

What is claimed is:

1. A system for measuring the glass transition temperature of a sample, the system comprising
    a load for providing a load force,
    a probe coupled to the load, the probe having a probe point for penetrating the sample, the load force being communicated through the probe,
    a heater for heating the sample,
    a temperature sensor for sensing the temperature of the sample during penetration, and
    a penetration sensor for sensing the amount of penetration of the probe point into the sample, the glass transition temperature being measured when the sample begins to change phase from a solid to a semisolid when being heated by the heater at which temperature the probe begins to penetrate the sample.

2. The system of claim 1 wherein,
    the probe has a sharpened point.

3. The system of claim 1 wherein, the temperature sensor is a thermocouple, the penetration sensor is an inductive transducer, and the probe is a steel probe.

4. The system of claim 1 wherein, the temperature sensor is a thermocouple, the penetration sensor is an inductive transducer, the probe is a steel probe with a sharpened point, and the load is a spring load.

5. The system of claim 1 wherein, the load force extends the probe beyond a retracing line defined by the heater, the retracing line defining a probe point position of zero penetration, and the heater makes contact with the sample for heating the sample to the glass transition temperature where the probe point extends beyond the retracing line by the penetration depth.

6. The system of claim 1 wherein, the sample comprises an epoxy resin.

7. The system of claim 1 wherein, the sample comprises a polymer resin.

8. The system of claim 1 wherein, the sample is a fiber reinforced composite material.

9. The system of claim 1 wherein, the load is a spring load.

10. The system of claim 1 further comprising, a processing means for recording the temperature from the temperature sensor and the penetration of the probe from the penetration sensor.

11. The system of claim 1 further comprising, a processing means for recording the temperature from the temperature sensor and the penetration of the probe from the penetration sensor and for determining the glass transition temperature of the sample at the temperature when the probe start penetration into the sample when the sample changes phases.

* * * * *